United States Patent [19]
Imaki et al.

[11] Patent Number: 4,562,207
[45] Date of Patent: Dec. 31, 1985

[54] PROSTAGLANDIN ANALOGUE

[75] Inventors: Katsuhiro Imaki, Tsuzuki; Takashi Muryobayashi, Takatsuki; Akiyoshi Kawasaki, Osaka, all of Japan

[73] Assignee: Ono Pharmaceutical Co., Ltd., Osaka, Japan

[21] Appl. No.: 587,634

[22] Filed: Mar. 8, 1984

[30] Foreign Application Priority Data

Mar. 8, 1983 [JP] Japan ................... 58-36625

[51] Int. Cl.$^4$ .................. C07C 177/00; A61K 31/557
[52] U.S. Cl. ..................... 514/573; 514/530; 560/118; 562/500; 549/415; 549/473; 536/46
[58] Field of Search ............. 424/305, 317; 560/118; 562/500; 514/530, 573; 549/415, 473

[56] References Cited

U.S. PATENT DOCUMENTS 4,278,688  7/1981  Hayashi ............... 424/305

FOREIGN PATENT DOCUMENTS 896274  9/1983  Belgium ............... 424/305

Primary Examiner—Robert Gerstl
Attorney, Agent, or Firm—Stevens, Davis, Miller & Mosher

[57] ABSTRACT

A novel prostaglandin analogue of the formula:

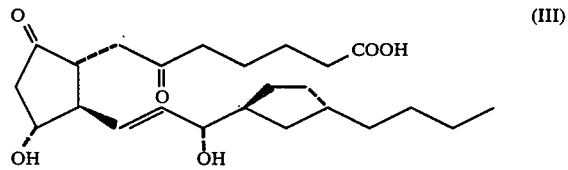

(III)

[wherein the symbol ⌁ represents $\beta$-configuration, the dotted line ———— represents $\alpha$-configuration, and the double bond between $C_{13}$–$C_{14}$ represents transconfiguration] and cyclodextrin clathrates thereof, and non-toxic salts thereof are useful for the treatment and/or prevention of diseases induced by platelet aggregation, such as thrombosis, or induced by cytodamage.

5 Claims, No Drawings

PROSTAGLANDIN ANALOGUE

The present invention relates to a novel prostaglandin $E_1$ analogue, a process for its preparation and pharmaceutical compositions containing it.

In the specification of our U.S. Pat. Nos. 4,215,142 and 4,278,688 and United Kingdom Pat. Nos. 2,006,753 and 2,079,268, we disclosed the prostaglandin analogues of the general formula:

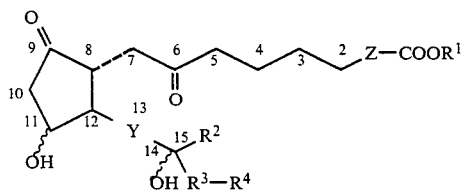
(I)

[wherein Y represents a trans-vinylene (i.e.

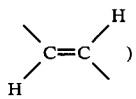
)

group or ethylene (i.e. $-CH_2CH_2-$) group, Z represents ethylene or trans-vinylene, $R^1$ represents a hydrogen atom, a straight- or branched-chain alkyl group containing from 1 to 12 carbon atoms, or a number of other esterifying moieties, $R^2$ represents a hydrogen atom, methyl group or ethyl group, $R^3$ represents a bond or a straight- or branched-chain alkylene group containing from 1 to 4 carbon atoms, $R^4$ represents a hydrogen atom or a straight- or branched-chain alkyl group containing from 1 to 8 carbon atoms, a cycloalkyl group containing from 4 to 7 carbon atoms in the ring and unsubstituted or substituted by at least one straight- or branched-chain alkyl group containing from 1 to 8 carbon atoms, or represents a phenyl or phenoxy group unsubstituted or substituted by at least one chlorine atom, trifluoromethyl group or an alkyl group containing from 1 to 3 carbon atom(s), and the wavy lines ~ attached to the C-11 and C-15 carbon atoms represent α- or β-configuration (i.e. $\underline{S}$ or $\underline{R}$-configuration) or mixture thereof] and cyclodextrin clathrates thereof, and when $R^1$ represents a hydrogen atom, non-toxic (e.g. sodium) salts thereof, which possess the valuable pharmacological properties typical of the prostaglandins in a selective fashion, in particular hypotensive activity, inhibitory activity on blood platelet aggregation, inhibitory activity on gastric acid secretion and gastric ulceration, stimulatory activity on uterine contraction and abortifacient, luteolytic and antinidatory activity, and are useful in the treatment of hypertension, in the treatment of disorders of the peripheral circulation, in the prevention and treatment of cerebral thrombosis and myocardial infarction, in the treatment of gastric ulceration, in the termination of pregnancy and induction of labour in pregnant female mammals, in the treatment of impaired fertility and in the control of oestrus, contraception and menstrual regulation in female mammals.

It has been discovered that the single prostaglandin analogue of the formula (I) wherein, Y represents trans-vinylene, Z represents ethylene, $R^1$ and $R^2$ both represent hydrogen atoms, $R_3$ represents a bond, and $R^4$ represents a group of the formula:

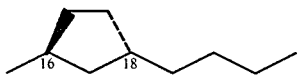
(II)

[wherein the symbol ▬ represents β-configuration, and the dotted line - - - represents α-configuration], and the hydroxy groups attached on the C-11 and C-15 carbon atoms are in α-configuration; i.e. 6-keto-16S,18S-ethano-20-ethyl-PGE$_1$, and cyclodextrin clathrates thereof and non-toxic salts thereof possess unexpectedly remarkable pharmacological properties.

The present invention accordingly provides the prostaglandin $E_1$ analogue of the formula:

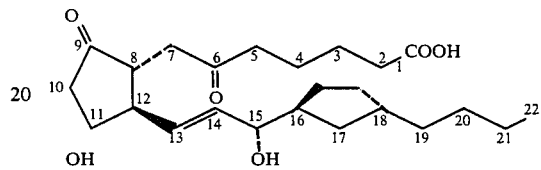
(III)

[wherein the symbol ▬ represents β-configuration, the dotted line - - - represents α-configuration, and the double bond between $C_{13}$–$C_{14}$ is in trans-configuration] and non-toxic salts thereof and cyclodextrin clathrates thereof.

It has been found that the prostaglandin analogue of the formula (III) possesses a very strong inhibitory activity on platelet aggregation, and therefore it is useful, for the treatment and/or prevention of diseases induced by platelet aggregation, for example angina pectoris, myocardial infarct, thrombosis and arteriosclerosis.

For example, the following Table shows the blood platelet aggregation-inhibiting activity of the compound of the present invention and that of a structurally related compound whose preparation is described in the specification of the U.S. Pat. No. 4,278,688. The platelet aggregation was induced by adenosine-diphosphoric acid (ADP) on human blood. The IC$_{50}$ values given in the Table are the concentrations which produce 50%-inhibition of platelet aggregation.

INHIBITING ACTIVITIES ON PLATELET AGGREGATION INDUCED BY ADP

| Compound | IC$_{50}$ (μg/ml) | Relative activity against PGE$_1$ |
|---|---|---|
| PGE$_1$ (control) | $3.45 \times 10^{-2}$ | 1.00 |
| ![structure with COOH] (Compound of the present invention) | $8.00 \times 10^{-5}$ | 431 |
| ![structure with COOCH$_3$] (Compound described in | $3.60 \times 10^{-3}$ | 9.58 |

| Compound | IC$_{50}$ ($\mu$g/ml) | Relative activity against PGE$_1$ |
|---|---|---|
| Example 2(d) of the specification of the U.S. Pat. No. 4,278,688.) | | |

It will be seen that the activity of the compound of the present invention is about 45 times as strong as that of the comparison compound disclosed specifically in the specification of the United States Patent: the compound of the present invention is therefore a very effective agent for combatting platelet aggregation.

It has also been discovered that the compound of the present invention possesses a new activity, i.e. cytoprotective activity, which is not described in the specification of the U.S. Pat. Nos. 4,215,412 and 4,278,688 and the United Kingdom Pat. Nos. 2,006,753 and 2,079,268.

The compound of the present invention exhibits a strong cytoprotective activity and may be used as a very effective preventing and/or treating agent for cytodamage (i.e. for the prevention and/or treatment of diseases associated with cytodamage).

The compound of the formula (III), cyclodextrin clathrates and non-toxic salts thereof are therefore useful for the prevention and/or the treatment of many diseases which are associated with cytodamage as follows:

(1) digestive system diseases (for example, liver diseases such as hepatitis, fatty liver, liver cirrhosis, liver abscess, pancreatic diseases such as pancreatitis)

(2) urologic diseases (for example, nephritis, diabetic nephropathies, cystitis, urethritis)

(3) respiratory tract diseases (for example, pneumonia, empyema, rhinitis)

(4) cardiovascular diseases (for example, arrhythmia, cerebral aneurysm, cerebral embolism)

(5) hemotologic diseases (for example, anemia)

(6) other diseases (for example, diabetes mellitus and complications caused by diabetes mellitus).

In standard laboratory tests, for example in carbon tetrachloride-induced liver damage in rats, 6-keto-16$\underline{S}$,18$\underline{S}$-ethano-20-ethyl-PGE$_1$, i.e. the compound of the present invention, produced 47% and 64% inhibition of plasma GOT (glutamic oxalacetic transaminase), and produced 42% and 66% inhibition of plasma GPT (glutamic pyruvic transaminase) by oral administration at the doses of 20 $\mu$g/kg and 50 $\mu$g/kg animal body weight in comparison with controls, respectively.

The experiments were carried out by the methods described in Example 1 of the specification of published W. German Patent Application No. 3310556.1 and Japanese Patent Kokai No. 58-164512, except that carbon tetrachloride was used as a 10% solution in olive oil.

The present invention includes the use of the compounds of the present invention in therapy in the prevention and/or treatment of diseases associated with cytodamage, described above.

The compound of the present invention may be prepared from a mixture of stereoisomers which may be prepared by the method described in the specification of the U.S. Pat. No. 4,278,688, by purification by conventional separation methods, e.g. high performance liquid, thin layer or column chromatography on silica gel or magnesium silicate, or known optical resolving methods [see Tables of Resolving Agents and Optical Resolutions, University of Notre Dame Press (1972)], and may also be prepared from an optically active isomer as a starting material by the preparative method described hereinafter.

According to a feature of the present invention, the prostaglandin analogue of the formula (III) may be prepared by the hydrolysis to hydroxy groups of the groups OR$^5$ of a compound of the general formula:

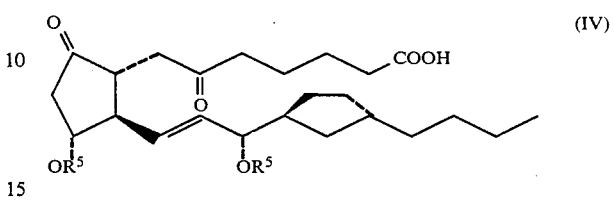

(IV)

[wherein R$^5$ represents a tetrahydropyran-2-yl group or a tetrahydrofuran-2-yl group, each such group being unsubstituted or substituted by at least one alkyl group, or represents a 1-ethoxyethyl group, and the other symbols are as defined above] under acidic conditions.

The hydrolysis may be carried out by known methods, for example, in an aqueous solution of an organic acid, e.g. acetic acid, propionic acid, oxalic acid, p-toluenesulphonic acid or an aqueous solution of an inorganic acid, e.g. hydrochloric acid, in the presence of a water-miscible solvent e.g. methanol, ethanol, dioxan or tetrahydrofuran, at a temperature of from ambient to 90° C.; preferably, it is carried out in a mixture of aqueous acetic acid and tetrahydrofuran, at about 80° C.

The compound of the formula (IV) may be prepared by oxidizing a compound of general formula:

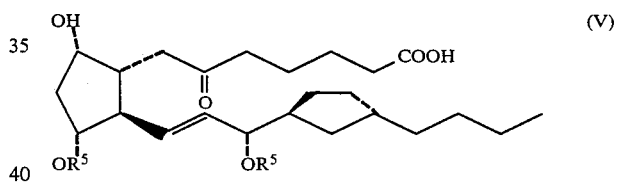

(V)

[wherein all of the symbols are as defined above.]

The oxidation may be carried out by known methods, for example, by oxidation with chromic acid, Collins oxidation or Jones oxidation; Jones oxidation is preferable.

The compound of the formula (V) may be prepared by saponifying a compound of general formula:

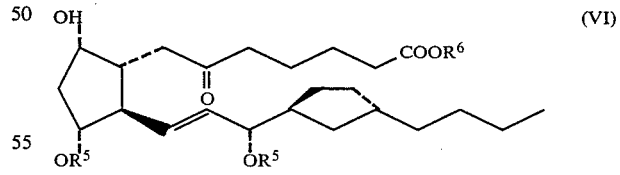

(VI)

[wherein, R$^6$ represents a straight- or branched-chain alkyl group containing from 1 to 4 carbon atom(s) and the other symbols are as defined above.]

The saponification may be carried out by known methods, for example, in an aqueous solution of alkali e.g. sodium hydroxide, potassium hydroxide, in the presence of water-miscible organic solvent e.g. methanol, ethanol, tetrahydrofuran, at a temperature of from 0° C.–40° C.; preferably, it is carried out in an aqueous solution of sodium hydroxide, in the presence of methanol, at ambient temperature.

The compound of the formula (VI) may be prepared by dehydrohalogenating a compound of general formula:

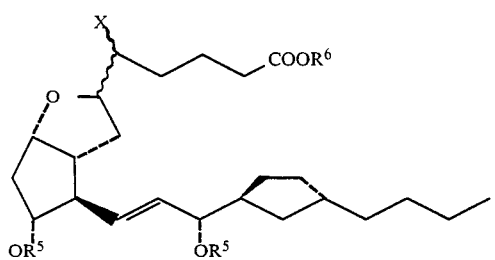

(VII)

[wherein, wavy lines ∼ represents α- or β-configuration or a mixture thereof, X represents a bromine or iodine atom, and the other symbols are as defined above] and then opening the ring of the resulting ester, by hydrolyzing under acidic condition.

The dehydrohalogenation may be carried out by known methods, for example, in an inert organic solvent e.g. toluene, benzene, using dehydrohalogenation agent e.g. 1,8-diazabicyclo[5.4.0]undecene-7 (DBU), 1,5-diazabicyclo[4.3.0]nonene-5 (DBN) or 1,4-diazabicyclo[2.2.0]octane (DABCO) at a temperature of from ambient to 110° C.; preferably, it is carried out in toluene, using 1,8-diazabicyclo[5.4.0]undecene-7 (DBU), at 50° C.–65° C.

The hydrolysis must be carried out carefully to avoid the elimination of $R^5$ groups on the 11- and 15-positions. Such hydrolysis is well known; preferably, it is carried out using hydrochloric acid.

The compound of the formula (VII) may be prepared by the introduction of protecting groups $R^5$ into a compound of the general formula:

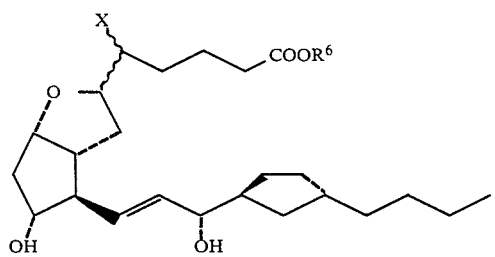

(VIII)

[wherein all of the symbols are as defined above.]

The introduction of the groups $R^5$ may be carried out by known methods, for example, in an inert organic solvent e.g. methylene chloride, chloroform, tetrahydrofuran, using 2,3-dihydropyran, 2,3-dihydrofuran, or ethyl vinyl ether, in the presence of acid catalyst, e.g. p-toluenesulphonic acid, benzenesulphonic acid, at a temperature of from −20° C. to ambient; preferably it is carried out in methylene chloride, in the presence of p-toluenesulphonic acid, at 0° C.

The compound of the formula (VIII) may be prepared by subjecting a compound of general formula:

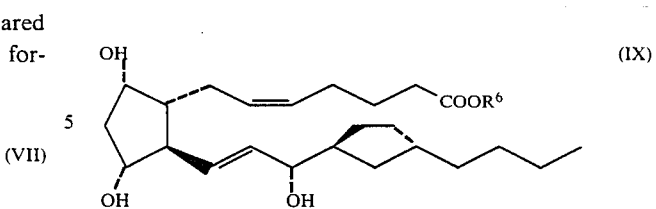

(IX)

[wherein, the double bond between $C_5$–$C_6$ represents cis-configuration, and all of the other symbols are as defined above] to a reaction wherein halogenation and cyclization are effected simultaneously.

The reaction of halogenation and cyclization at the same time may be carried in the following manner: (i) when X of the compound of the general formula (VIII) represents an iodine atom, the reaction is effected by using iodine in pyridine at a temperature of from ambient to 0° C. or by using iodine in an inert organic solvent such as methylene chloride or chloroform in the presence of a carbonate of an alkali metal such as sodium or potassium or in the presence of a bicarbonate of an alkaline earth metal such as calcium, or magnesium, at a temperature of from ambient to 0° C.; or (ii) when X of the compound of the general formula (VIII) represents a bromine atom, the reaction is effected by using N-bromosuccinimide or N-bromoacetamide in a non-protonic organic solvent, for example, methylene chloride, chloroform, carbon tetrachloride, diethyl ether, N,N-dimethylformamide, tetrahydrofuran or a mixed solvent thereof at a temperature of from −30° C. to 70° C. Preferably, it is effected by adding a saturated aqueous solution of sodium bicarbonate to a methylene chloride solution of the compound of the general formula (IX) and adding slowly and dropwise a methylene chloride solution of iodine at 0° C.; preferably, it is carried out, in chloroform, in the presence of tetrahydrofuran, using N-bromosuccinimide.

The compound of the formula (IX) may be prepared by removal of the $R^7$ group of a compound of general formula:

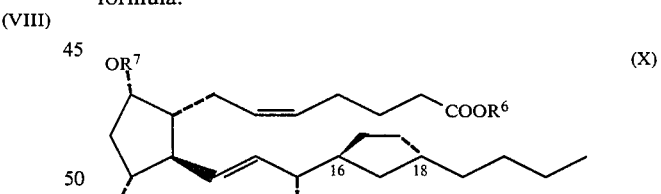

(X)

[wherein, $R^7$ represents a straight- or branched-chain alkanoyl group containing from 2 to 5 carbon atoms and all the other symbols are as defined above].

The removal of the group $R^7$ may be carried out by known methods, for example, in anhydrous conditions, in an inert organic solvent, e.g. anhydrous methanol, in the presence of catalyst, e.g. anhydrous potassium carbonate, anhydrous sodium carbonate, at a temperature of from 0° C. to 40° C.; preferably, it is carried out in anhydrous methanol, using anhydrous potassium carbonate, at ambient temperature.

The compound of the formula (X) may be prepared by separating a mixture of two isomers (i.e. a mixture of 16R-conformation isomer and 16S-conformation isomer) of general formula:

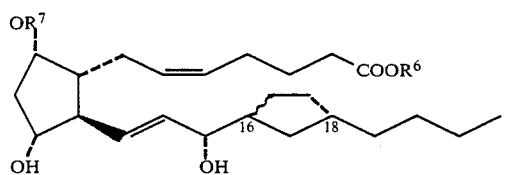
(XI)

[wherein all the symbols are as defined above].

The separation may be carried out by known method e.g. column chromatography on silica gel or magnesium silicate; preferably it is carried out by Lobar column chromatography (produced by Merck & Co., Ltd.).

The compound of the formula (XI) may be prepared by removal of the $R^8$ group from a compound of general formula:

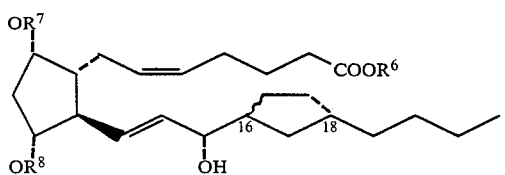
(XII)

[wherein $R^8$ represents a tetrahydropyran-2-yl group or a tetrahydrofuran-2-yl group, each such group being unsubstituted or substituted by at least one alkyl group, or represents a 1-ethoxyethyl group, and the other symbols are as defined above].

The removal of the $R^8$ group may be carried out by known methods, for example, in an inert organic solvent, e.g. methanol, dioxan, tetrahydrofuran, using a catalyst e.g. pyridinium p-toluenesulphonate, at a temperature of from ambient to 70° C.; preferably, it is carried out in methanol, using pyridinium p-toluenesulphonate, at 50° C.

The compound of the formula (XII) may be prepared by reducing a compound of general formula:

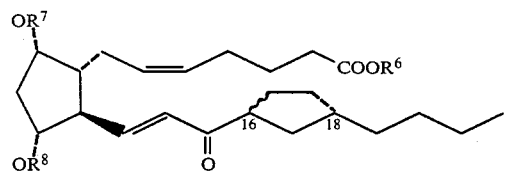
(XIII)

[wherein all the symbols are as defined above].

The reduction may be carried out by known methods, for example, under an atmosphere of inert gas, e.g. argon, in an anhydrous organic solvent, e.g. anhydrous toluene or tetrahydrofuran using as reducing agent, e.g. diisobutyl aluminium hydride (DIBAL), in the presence or absence of 3,5-di-t-butyl-4-hydroxytoluene, or Noyori's reagent prepared by reaction of lithium aluminium hydride, (S)-2,2'-dihydroxy-1,1'-binaphthyl and ethanol at a temperature of from −78° C. to −15° C.; preferably it is carried out using diisobutyl aluminium hydride in the presence of 3,5-di-t-butyl-4-hydroxytoluene at −78° C.

The compound of the formula (XIII) may be prepared by subjecting a compound of general formula:

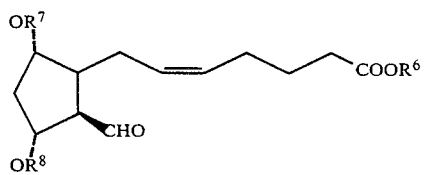
(XIV)

[wherein all the symbols are as defined above] and a compound of general formula:

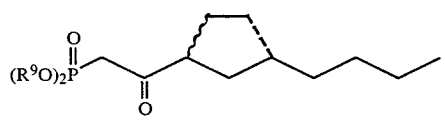
(XV)

[wherein $R^9$ represents a straight- or branched-chain alkyl group containing from 1 to 4 carbon atoms or a phenyl group, and the other symbols are as defined above] to the Wittig reaction.

The Wittig reaction is a known reaction, carried out, for example, under atmosphere of inert gas, e.g. argon, in anhydrous conditions, in an inert organic solvent e.g. tetrahydrofuran, benzene, hexane, in the presence of sodium hydride, at −78° C.; preferably it is carried out in tetrahydrofuran in the presence of sodium hydride.

The compound of the formula (XIV) is a known compound; for example, a compound of the formula (XIV) wherein $R^8$ represents tetrahydropyran-2-yl group, $R^6$ represents methyl group and $R^7$ represents acetyl group may be prepared by the method described in Example 12 in the specification of the United Kingdom Pat. No. 1,482,928.

The compound of the general formula (XV) may be prepared by the series of reactions described in the following Scheme A.

In each formula of Scheme A, the symbol $\phi$ represents a phenyl group, $T^1$ and $T^2$ represent a tosyl group, i.e. a p-toluenesulphonyl group or a mesyl group, i.e. a methylsulphonyl group, $R^{10}$ and $R^{12}$ represent a straight- or branched-chain alkyl group containing from 1 to 4 carbon atom(s), independently, $R^{11}$ represents a tetrahydropyran-2-yl group or a tetrahydrofuran-2-yl group, each such group being unsubstituted or substituted by at least one alkyl group or represents a 1-ethoxyethyl group, and the other symbols are as defined above.

SCHEME A

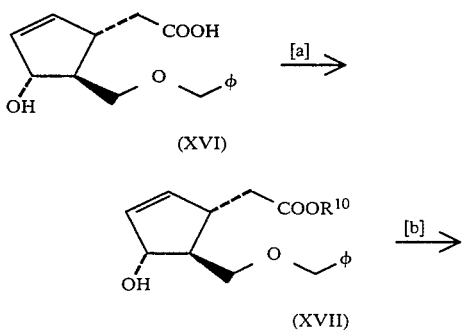

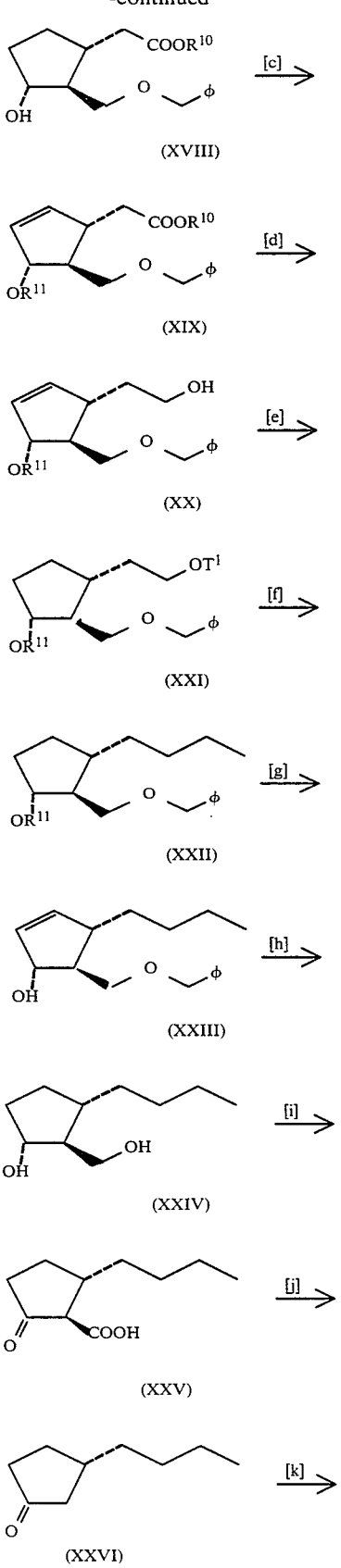

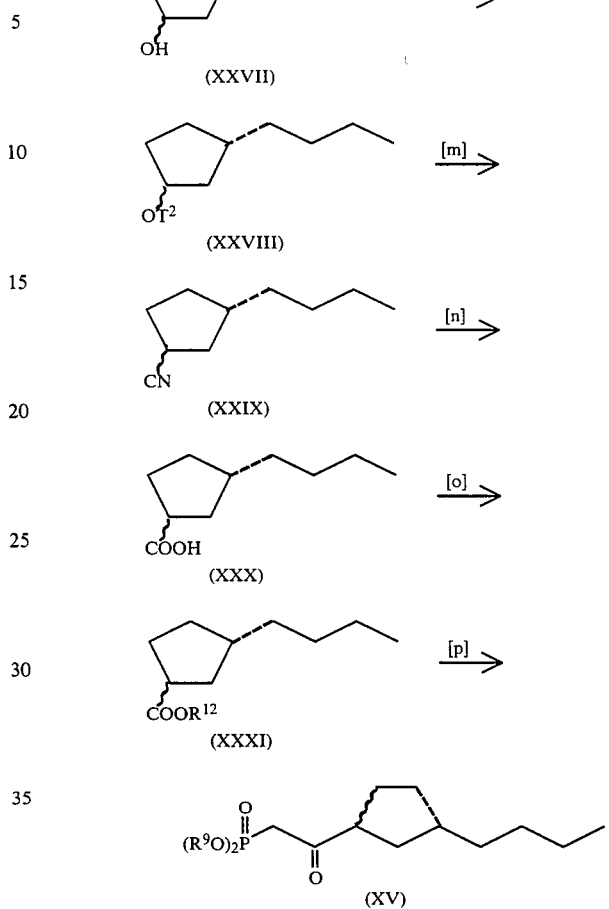

Each step in Scheme A is carried out by known methods; a brief description of each step follows. Step (a) is esterification, and is carried out (1) using methyl iodide, in the presence of anhydrous sodium carbonate in acetone at a temperature of from 0° C. to 40° C. (preferably at ambient temperature), or (2) using a diazoalkane, e.g. diazomethane in an organic solvent e.g. diethyl ether, methanol, ethanol, at a temperature of from −20° C. to 20° C.

Step (b) is reduction, and is carried out in an atmosphere of hydrogen, using a catalyst e.g. platinum oxide, palladium, palladium-carbon, platinum, nickel in diethyl ether, methanol, at a temperature of from 0° C. to 40° C. (preferably at ambient temperature).

Step (c) is an addition reaction introducing $R^{11}$ and is carried out using 2,3-dihydropyran, 2,3-dihydrofuran, or ethyl vinyl ether in the presence of p-toluenesulphonic acid, in methylene chloride, at a temperature of from −10° C. to 40° C.

Step (d) is reduction, and is carried out in anhydrous conditions at a temperature of from −40° C. to 20° C. using diisobutyl aluminium hydride (DIBAL) or lithium aluminium hydride in toluene, diethyl ether, or tetrahydrofuran.

Step (e) is tosylation or mesylation, and is carried out using p-toluenesulphonyl chloride or mesyl chloride in pyridine or triethylamine at a temperature of from −20° C. to ambient.

Step (f) is a replacement reaction, and is carried out using e.g. an ethyl magnesium halide, in the presence of catalyst, e.g. a mixture of cupric chloride and lithium chloride, in an ether e.g. tetrahydrofuran, diethyl ether, or mixture thereof, at a temperature of from −78° C. to ambient.

Step (g) is removal of the $R^{11}$ group, and is carried out at a temperature of from ambient to 60° C. (preferably at 40° C.), using pyridinium p-toluenesulphonate in methanol, or using acid catalyst, e.g. hydrochloric acid in tetrahydrofuran, or using an aqueous solution of acetic acid.

Step (h) is debenzylation and is carried out under a hydrogen atmosphere, using a catalyst, e.g. palladium-carbon, palladium, platinum, nickel, in a mixture of acetic acid and ethyl acetate, methanol or ethanol and at a temperature of from 0° C. to 40° C., preferably at ambient temperature.

Step (i) is oxidation, and is carried out, using Jones reagent in acetone, at a temperature of from −10° C. to ambient, preferably at 0° C.

Step (j) is a reaction of decarboxylation, and is carried out by heating at a temperature of from 80° C. to 160° C. in the absence or in the presence of dilute sulphuric acid, preferably only heating at a temperature of from 100° C. to 140° C.

Step (k) is reduction, and is carried out, using sodium borohydride ($NaBH_4$) in methanol, or DIBAL in toluene at a temperature of from −30° C. to ambient, preferably at 0° C.

Step (l) is tosylation or mesylation, and is carried out as the method described in step (e), previously.

Step (m) is cyanogenation, and is carried out, using sodium cyanide, in dimethylsulphoxide at a temperature of from 40° C. to 70° C., preferably at 50° C.

Step (n) is hydrolysis and is carried out using an acid, preferably a mixture of sulphuric acid and acetic acid, and water, or conc. hydrochloric acid in dioxan at a temperature of from 80° C. to 130° C., preferably 110° C.

Step (o) is esterification, and is carried out as the method described in step (a) previously.

Step (p), conversion into a Wittig reagent, is carried out using a reagent of general formula:

$(R^9O)_2(CH_3)P=O$, in the presence of n-butyl lithium, in a mixture of hexane and tetrahydrofuran, at a temperature of from −78° C. to ambient.

The compound of the formula (XVI) is a known compound; for example, it may be prepared by the method described in J. Am. Chem. Soc., 93, 1492 (1971).

The Wittig reagent of the general formula (XV) may also be prepared by an alternate route depicted in the following Scheme B. In using this synthetic route the Wittig reagent of general formula (XVa) wherein the configuration at the $C_{16}$-position is S, may be easily obtained. The compound of the present invention of the formula (III) can then be obtained in good yield, as the difficult separation step i.e. the preparation step of the 16S-compounds of the general formula (X) from the 16$\underline{RS}$-compounds of the general formula (XI), is not required.

In the following Scheme B, the symbol  represents a t-butyl group, $T^3$ represents a tosyl group or mesyl group, and $R^{9a}$ represents a straight- or branched-chain alkyl group containing from 1 to 4 carbon atom(s).

SCHEME B

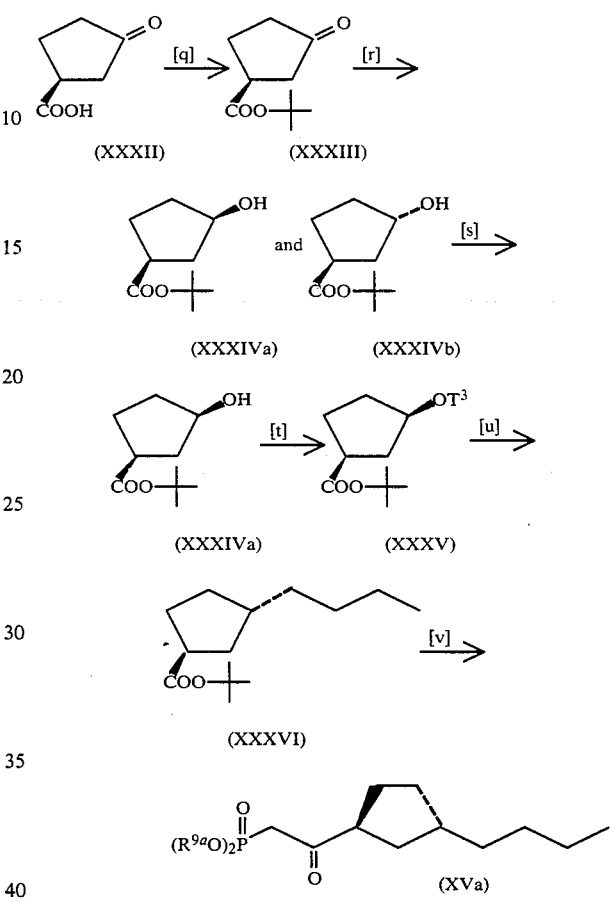

In scheme B, each step can be effected using methods known per se. For example, step (q) may be carried out by esterification for example, using isobutene in the presence of sulphuric acid in an inert organic solvent e.g. methylene chloride, chloroform, tetrahydrofuran, or using t-butanol, in the presence of dicyclohexylcarbodiimide (DCC) and dimethylaminopyridine at a temperature of from −20° C. to 50° C.

Step (r) may be carried out by reduction, for example, at a temperature of from −70° C. to 50° C., using sodium borohydride, in an organic solvent, e.g. methanol, ethanol, tetrahydrofuran, or using lithium aluminium tri-tert-butoxy hydride in an organic solvent e.g. tetrahydrofuran or diethyl ether. By the reduction, the compound of the formula (XXXIVa) may be obtained as major product in a resulting mixture.

Step (s) is separation, and is carried by conventional methods, for example, using high performance liquid chromatography, thin layer chromatography or column chromatography using silica gel or magnesium silicate.

Step (t) is tosylation or mesylation, and is carried out as the method described in step (e) of scheme A, previously.

Step (u) is alkylation, and is carried out, for example, in anhydrous conditions, using an alkylating agent, e.g. Grignard reagent, lithium alkylate, in the absence or presence of catalyst, e.g. cupric chloride and lithium chloride, in ether, e.g. tetrahydrofuran, diethyl ether, at a temperature of from −78° C. to ambient.

Step (v), conversion into a Wittig reagent, is carried out as the method described in step (p) of Scheme A, previously.

The compound of the formula (XXXII) is a known compound; for example, it may be prepared by the method described in Bull. Chem. Soc. Jpn., 31, 333 (1958).

Cyclodextrin clathrates of the prostaglandin $E_1$ analogue of the formula (III) may be obtained by the method described in the specification of the United Kingdom Patent Nos. 1,351,238 or 1,419,221 using α-, β- or γ-cyclodextrin, or a mixture thereof.

Conversion into its cyclodextrin clathrates increases the stability and water solubility of the prostaglandin $E_1$ analogue of the formula (III).

Salts can be obtained from the prostaglandin $E_1$ analogue of the formula (III) by known methods, for example by reacting the compound of the formula (III) and a suitable base, such as a hydroxide or carbonate of an alkali metal or alkaline earth metal, ammonium hydroxide, ammonia or an organic amine in theoretical amounts in an appropriate solvent. The salt can be isolated by freeze-drying the solution, or by filtration if the salt is sufficiently insoluble in the reaction solvent, or, if necessary by removing part of the solvent followed by filtration. The salts are preferably non-toxic salts. By the term "non-toxic salts" as used in this specification is meant salts the cations of which are relatively innocuous to animal tissues when used in therapeutic doses so that the beneficial pharmacological properties of the prostaglandin $E_1$ analogue of formula (III) are not impaired by side effects resulting from the cation. It is preferable that the salts are water-soluble. Suitable salts include, for example, a salt of an alkali metal such as sodium or potassium, a salt of an alkaline earth metal such as calcium or magnesium, an ammonium salt and a pharmaceutically acceptable (non-toxic) amine salt. Amines suitable for forming such a salt with a carboxylic acid are well known, and include, for example, those amines which are theoretically obtained by substituting one or more hydrogen atoms of ammonia by other groups. These groups, which may be the same or different from each other when one or more hydrogen atoms are substituted, are selected from, for example, alkyl groups of 1-6 carbon atoms and hydroxyalkyl groups of 2-3 carbon atoms. Suitable non-toxic amine salts include tetraalkylammonium salts, such as tetramethylammonium salts and salts of an organic amine, such as methylamine, dimethylamine, cyclopentylamine, benzylamine, phenethylamine, piperidine, monoethanolamine, diethanolamine, lysine, and arginine.

The toxicity of the compound of the present invention is very weak, and therefore, the compound of the present invention is sufficiently safe for use as a pharmaceutical.

For example, in a test of acute toxicity in mice by oral administration, the value of $LD_{50}$ of 6-keto-16$\underline{S}$,18$\underline{S}$-ethano-20-ethyl-PGE$_1$ for the compound of the present invention is very large; that is the value is more than 3 mg/kg animal body weight.

The following Reference Examples and Examples illustrate the preparation of compounds of the present invention. In the Reference Examples and Examples, 'mp', 'TLC', 'IR', 'NMR' and 'Mass' represent 'melting point', 'Thin layer chromatography', 'Infrared absorption spectrum', 'Nuclear magnetic resonance' and 'Mass spectrum', respectively. Where solvent ratios are specified in chromatographic separations, the ratios are by volume: the solvents in parentheses in thin layer chromatography show the developing solvents used. Except when specified otherwise, infrared spectra are recorded by the liquid film method and nuclear magnetic resonance spectra are recorded in deuterochloroform ($CDCl_3$) solution.

REFERENCE EXAMPLE 1

(1$\underline{S}$,2$\underline{S}$,3$\underline{S}$)-2-benzyloxymethyl-3-methoxycarbonylmethyl-4-cyclopenten-1-ol To a solution of 23.6 g of (1$\underline{S}$,2$\underline{S}$,3$\underline{S}$)-2-benzyloxymethyl-3-carboxymethyl-4-cyclopenten-1-ol [the compound described in J. Am. Chem. Soc., 93, 1492 (1971)] in 200 ml of acetone, 27.6 g of potassium carbonate and 11.36 g of methyl iodide were added. The mixture was stirred for 50 min at room temperature, and then refluxed for 2 hrs. After reacting, the mixture was filtered and the filtrate was concentrated under reduced pressure. The residue was purified by column chromatography on silica gel using a mixture of cyclohexane and ethyl acetate (2:1) as eluent to give 24.9 g of the title compound having the following physical characteristics, in a 99% yield.

TLC (cyclohexane:ethyl acetate=1:1): Rf=0.68.

IR: $\nu$=3400, 1740, 1455, 1440, 1368, 1171, 1100, 743, 705 cm$^{-1}$.

NMR: $\delta$=7.20(5H, s), 5.67(2H, s), 4.55(1H, m), 4.47(2H, s), 3.58(3H, s).

REFERENCE EXAMPLE 2

(1$\underline{R}$,2$\underline{S}$,3$\underline{S}$)-2-benzyloxymethyl-3-methoxycarbonylmethylcyclopentan-1-ol In an atmosphere of hydrogen, a mixture of 10.0 g of (1$\underline{S}$,2$\underline{S}$,3$\underline{S}$)-2-benzyloxymethyl-3-methoxycarbonylmethyl-4-cyclopenten-1-ol (prepared in Reference Example 1), 60.0 mg of platinum oxide and 50 ml of diethyl ether was stirred for 2.5 hrs at room temperature. The mixture was filtered for removing platinum oxide. The filtrate was concentrated under reduced pressure. The residue was purified by column chromatography on silica gel using a mixture of cyclohexane and ethyl acetate (2:1) as eluent to give 8.55 of the title compound having the following physical characteristics, in a 85% yield.

TLC (cyclohexane:ethyl acetate=2:1): Rf=0.29.

IR: $\nu$=3450, 2950, 2860, 1735, 1435 cm$^{-1}$.

NMR: $\delta$=7.30(5H, s), 4.50(2H, s), 4.04(1H, m), 3.62(3H, s), 3.58(1H, t), 3.39(1H, t), 2.56(1H, bs), 2.40(2H, dd), 1.38–2.10(6H, m).

Mass: m/e=278(M$^+$), 260, 247, 187, 169, 154, 137, 122, 107, 91.

REFERENCE EXAMPLE 3

(1$\underline{R}$,2$\underline{S}$,3$\underline{S}$)-2-benzyloxymethyl-3-methoxycarbonylmethyl-1-(2-tetrahydropyranyloxy)cyclopentane A mixture of 8.52 g of (1$\underline{R}$,2$\underline{S}$,3$\underline{S}$)-2-benzyloxymethyl-3-methoxycarbonylmethylcyclopentan-1-ol (prepared in Reference Example 2), 7.4 ml of 2,3-dihydropyran and 30 ml of methylene chloride was prepared and then cooled. To the mixture 370 mg of p-toluenesulphonic acid monohydrate was added, the mixture was stirred for 20 min. at 0° C., and for 30 min. at room temperature. After addition of 1 ml of pyridine, the mixture was diluted with 300 ml of diethyl ether. The diluted solution was washed with water, dilute hydrochloric acid, an aqueous solution of sodium bicarbonate and water successively, dried over anhydrous magnesium sulphate and concentrated under reduced pressure to give 14.2 g of the title compound having the following physical characteristics.

TLC (cyclohexane:ethyl acetate=2:1): Rf=0.57.
Mass: m/e=362(M+), 331, 277, 259, 247, 229, 199, 187, 171, 169, 154, 137, 107, 91, 85.

REFERENCE EXAMPLE 4

(1R,2S,3S)-2-benzyloxymethyl-3-(2-hydroxyethyl)-1-(2-tetrahydropyranyloxy)cyclopentane In a flow of argon, to a solution cooled to −15° C., of 14.2 g of (1R,2S,3S)-2-benzyloxymethyl-3-methoxycarbonylmethyl-1-(2-tetrahydropyranyloxy)cyclopentane (prepared in Reference Example 3) in 100 ml of dry toluene, 42 ml of a 25% solution of DIBAL (diisobutyl aluminium hydride) in toluene was added dropwise. The mixture was stirred for 2 hrs, and then 20 ml of methanol was added thereto at the same temperature. The solution was stirred at room temperature and, after deposition of aluminum hydroxide, magnesium sulphate was added thereto. The mixture was filtered, and the filtrate was concentrated under reduced pressure. The residue was purified by column chromatography on silica gel using a mixture of cyclohexane and ethyl acetate (2:1) as eluent to give 10.3 g of the title compound having the following physical characteristics.

TLC (cyclohexane:ethyl acetate=2:1): Rf=0.23.
IR: $\nu$=3450, 2935, 2860, 1450, 1360 cm$^{-1}$.
Mass: m/e=334(M+), 316, 249, 231, 159, 141, 125, 108, 91, 85.

REFERENCE EXAMPLE 5

(1R,2S,3S)-2-benzyloxymethyl-1-(2-tetrahydropyranyloxy)-2-[2-(p-toluenesulphonyloxy)ethyl]cyclopentane To a solution cooled with ice-water, of 10.3 g of (1R,2S,3S)-2-benzyloxymethyl-3-(2-hydroxyethyl)-1-(2-tetrahydropyranyloxy)cyclopentane (prepared in Reference Example 4) in 60 ml of pyridine, 11.8 g of p-toluenesulphonyl chloride was added, and the mixture was stirred for 5 hrs at the same temperature. After reaction, the solution was diluted with 1 l of ethyl acetate; the diluted solution was washed with dilute hydrochloric acid, water and a saturated aqueous solution of sodium chloride, successively, dried over magnesium sulphate and concentrated under reduced pressure. The residue was purified by column chromatography on silica gel using a mixture of cyclohexane and ethyl acetate (3:1) as eluent to give 13.6 g of the title compound having the following physical characteristics in a 90% yield.

TLC (cyclohexane:ethyl acetate=2:1): Rf=0.56.
IR: $\nu$=2930, 2860, 1360 cm$^{-1}$.
NMR: $\delta$=7.20–7.40(9H, bs), 4.52(2H, s), 2.04(3H, s).
Mass: m/e=403, 386, 368, 280, 232, 214, 196, 172, 141, 125, 107.

REFERENCE EXAMPLE 6

(1R,2S,3S)-2-benzyloxymethyl-3-butyl-1-(2-tetrahydropyranyloxy)cyclopentane

In a flow of argon, to a solution cooled to −78° C., of 13.6 g of (1R,2S,3S)-2-benzyloxymethyl-1-(2-tetrahydropyranyloxy)-3-[2-(p-toluenesulphonyloxy)ethyl]cyclopentane (prepared in Reference Example 5) in 30 ml of dry tetrahydrofuran, 12.5 ml of a 3M solution of ethyl magnesium bromide in diethyl ether was added over a period of 10 min; to the solution, 5 ml of a solution of 8.4 g of lithium chloride and 13.4 g of cupric chloride in 1 l of tetrahydrofuran was added dropwise over a period of 5 min. The mixture was stirred further for 1.5 hrs at the same temperature, for 2 hrs at 0° C., and for 16 hrs at room temperature. The reaction solution was poured into a mixture of 70 ml of 1N hydrochloric acid, ice and 150 ml of diethyl ether, and the ether layer separated was washed with an aqueous solution of sodium bicarbonate and a saturated aqueous solution of sodium chloride, successively, dried over anhydrous magnesium sulphate, and concentrated under reduced pressure. The residue was purified by column chromatography on silica gel using a mixture of cyclohexane and ethyl acetate (5:1) as eluent to give 8.63 g of the title compound having the following physical characteristics, in a 89.8% yield.

TLC (cyclohexane:ethyl acetate=2:1): Rf=0.68.
IR: $\nu$=2930, 2860, 1450, 1360 cm$^{-1}$.
NMR: $\delta$=7.32(5H, bs), 4.64(1H, m), 4.55(2H, s), 3.96–4.18 (1H, m), 3.75–3.96(1H, m), 3.26–3.60(3H, m), 1.12–1.94(18H, m), 0.88(3H, t).
Mass: m/e=346(M+), 261, 244, 227, 169, 153, 137, 107, 101, 91, 85.

REFERENCE EXAMPLE 7

(1R,2S,3S)-2-benzyloxymethyl-3-butylcyclopentan-1-ol

A mixture of 8.57 g of (1R,2S,3S)-2-benzyloxymethyl-3-butyl-1-(2-tetrahydropyranyloxy)cyclopentane (prepared in Reference Example 6), 50 ml of tetrahydrofuran and 25 ml of 2N hydrochloric acid was stirred for 2.5 hrs at 40° C. The mixture was extracted with 150 ml of diethyl ether, and the extract was washed with an aqueous solution of sodium bicarbonate and a saturated aqueous solution of sodium chloride successively, dried over anhydrous magnesium sulphate, and concentrated under reduced pressure. The residue was purified by column chromatography on silica gel using a mixture of cyclohexane and ethyl acetate (3:1) as eluent to give 4.31 g of the title compound having the following physical characteristics, in a 66.4% yield.

TLC (cyclohexane:ethyl acetate=2:1): Rf=0.42.
IR: $\nu$=3440, 2925, 2850, 1450, 1360 cm$^{-1}$.
NMR: $\delta$=7.32(5H, bs), 4.52(2H, q), 4.03(1H, m), 3.66(1H, dd), 3.55(1H, t), 2.58(1H, bs), 1.10–1.98(11H, m), 0.87 (3H, t).
Mass: m/e=262(M+), 244, 200, 171, 154, 138, 120, 107, 91.

REFERENCE EXAMPLE 8

(1R,2S,3S)-3-butyl-2-hydroxymethylcyclopentan-1-ol

In an atmosphere of hydrogen, a mixture of 4.29 g of (1R,2S,3S)-2-benzyloxymethyl-3-butylcyclopentan-1-ol (prepared in Reference Example 7), 500 ml of 10% palladium-carbon, 20 ml of ethyl acetate and 10 ml of acetic acid was stirred for 16 hrs at room temperature. After stirring the reaction mixture was filtered and the filtrate was concentrated under reduced pressure. The residue was purified by column chromatography on silica gel using a mixture of cyclohexane and ethyl acetate (1:3) as eluent to give 2.59 g of the title compound having the following physical characteristics in a 91.8% yield.

TLC (cyclohexane:ethyl acetate=1:3): Rf=0.30.
IR: $\nu$=3350, 2925, 2850, 1460 cm$^{-1}$.

NMR: δ=4.06(1H, m), 3.86(1H, dd), 3.30(1H, t), 2.90(2H, bs), 1.10-2.00(11H, m), 0.88(3H, t).
Mass: m/e=154, 139, 136, 125, 110, 97, 68.

REFERENCE EXAMPLE 9

(1R,5S)-5-butyl-2-oxocyclopentane-1-carboxylic acid

To a solution cooled with ice, of 2.07 g of (1R,2S,3S)-3-butyl-2-hydroxymethylcyclopenta-1-ol (prepared in Reference Example 8) in 40 ml of acetone, 15.2 ml of Jones reagent (a 25 ml solution was prepared as follows: 6.65 g of chromium trioxide was dissolved in 5.8 ml of conc. sulphuric acid, and then sufficient distilled water was added thereto to obtain a 25 ml solution) was added dropwise, and the mixture was stirred for 1.5 hrs at the same temperature. After addition of 100 ml of ice-water, the mixture was extracted with diethyl ether. The oily layer was washed with water, dried over anhydrous magnesium sulphate, and concentrated under reduced pressure to give 1.71 g of the title compound having the following physical characteristics, in a 81.9% yield.

TLC (cyclohexane:ethyl acetate=1:3): Rf=0.38.
Mass: m/e=184(M+), 170, 167, 152, 142, 139, 132, 127, 114.

REFERENCE EXAMPLE 10

3S-butylcyclopentanone 1.71 g of (1R,5S)-5-butyl-2-oxocyclopentane-1-carboxylic acid (prepared in Reference Example 9) was heated with stirring for 30 min. at 100° C. and for 3 hrs at 140° C. After cooling, the product was diluted with 30 ml of diethyl ether, the solution was washed with water, dried over anhydrous magnesium sulphate, and purified by vacuum distillation. The fraction of from 150° C. to 170° C. at 35 mm/Hg was purified by column chromatography on silica gel using a mixture of cyclohexane and ethyl acetate (3:1) as eluent to give 152 mg of the title compound having the following physical characteristics.

TLC (cyclohexane:ethyl acetate=2:1): Rf=0.54.
NMR: δ=2.01-2.49(4H, m), 1.71-1.92(1H, m), 1.20-1.66(8H, m), 0.91(3H, t).

REFERENCE EXAMPLE 11

(1RS,3S)-3-butylcyclopentan-1-ol

To a solution cooled with ice, of 120 mg of 3S-butylcyclopentanone (prepared in Reference Example 10) in 2 ml of methanol, 35 mg of sodium borohydride was added, and the mixture was stirred for 1 hr at the same temperature. After neutralizing with acetic acid, the mixture was concentrated under reduced pressure. The residue was diluted with ethyl acetate. The diluted solution was washed with water, dried over anhydrous magnesium sulphate, and concentrated under reduced pressure to give 94 mg of the title compound having the following physical characteristic, in a 77.2% yield.

TLC (cyclohexane:ethyl acetate=1:2): Rf=0.40.

REFERENCE EXAMPLE 12

(1S,3RS)-1-butyl-3-(p-toluenesulphonyloxy)cyclopentane

To a solution cooled with ice, of 94 mg of (1RS,3S)-3-butylcyclopentan-1-ol (prepared in Reference Example 11) in 2 ml of pyridine, 260 mg of p-toluenesulphonyl chloride was added, and the mixture was stirred for 30 min. at the same temperature and for 5 hrs at room temperature. The reaction solution was poured into ice-water. The mixture was extracted with a mixture of pentane and diethyl ether (1:1). The extract was washed with water, dried over magnesium sulphate, and concentrated under ambient pressure at 50° C. to give 190 mg of the title compound having the following physical characteristic.

TLC (cyclohexane:ethyl acetate=1:2): Rf=0.67.

REFERENCE EXAMPLE 13

(1RS,3S)-3-butyl-1-cyanocyclopentane

A mixture of 190 mg of (1S,3RS)-1-butyl-3-(p-toluene-sulphonyloxy)cyclopentane (prepared in Reference Example 12), 150 mg of sodium cyanide and 1.5 ml of anhydrous dimethyl sulphoxide was stirred for 30 mins. at 50° C. After diluting with 3 ml of water, the mixture was extracted with 10 ml of a mixture of pentane and diethyl ether (1:1). The extract was washed with water and a saturated aqueous solution of sodium chloride, successively, dried over anhydrous magnesium sulphate, and concentrated under ambient pressure at 50° C. The residue was purified by column chromatography on silica gel using a mixture of hexane and ethyl acetate (1:3) as eluent to give 73 mg of the title compound having the following physical characteristics.

TLC (cyclohexane:ethyl acetate=1:2): Rf=0.74.
IR (chloroform solution): ν=2960, 2925, 2860, 2240 cm$^{-1}$.
Mass: m/e=151(M+), 123, 109, 97, 80, 66.

REFERENCE EXAMPLE 14

(1RS,3S)-3-butylcyclopentanecarboxylic acid

A mixture of 73 mg of (1RS,3S)-3-butyl-1-cyanocyclopentane (prepared in Reference Example 13), 0.6 ml of conc. sulphuric acid, 0.6 ml of acetic acid and 0.6 ml of water was stirred for 1 hr. at 110° C. To the reaction solution, 30 ml of ethyl acetate and 20 ml of water were added. The oily layer which separated was washed with water, dried over anhydrous magnesium sulphate, and concentrated under reduced pressure. The residue was purified by column chromatography on silica gel using a mixture of cyclohexane and ethyl acetate (2:1) as eluent to give 30 mg of the title compound having the following physical characteristics, in a 36.5% yield.

TLC (cyclohexane:ethyl acetate=2:1): Rf=0.60.
Mass: m/e=170(M+), 152, 141, 128, 101, 98, 95.

REFERENCE EXAMPLE 15

(1RS,3S)-3-butylcyclopentane-1-carboxylic acid methyl ester

A mixture of 84 mg of (1RS,3S)-3-butylcyclopentanecarboxylic acid (prepared in Reference Example 14) and 1.0 ml of a 1M solution of diazomethane in diethyl ether was stirred with cooling. The mixture was concentrated under ambient pressure to give 72 mg of the title compound having the following physical characteristic.

TLC (ethyl acetate:cyclohexane=2:1): Rf=0.63.

REFERENCE EXAMPLE 16 dimethyl 2-(3S-butylcyclopentyl)-2-oxoethylphosphonate

In a flow of argon, to a solution of 250 mg of dimethyl methylphosphonate in 1 ml of tetrahydrofuran, 0.7 ml of a 1.5M solution of n-butyl lithium in hexane was added dropwise at −78° C., and the mixture was stirred for 30 min. at the same temperature. To the solution, 72 mg of (1RS,3S)-3-butylcyclopentane-1-carboxylic acid methyl ester (prepared in Reference Example 15) was added dropwise at −78° C. The mixture was stirred for 30 min. at the same temperature and then gradually warmed to room temperature with stirring. After addition of 0.5 ml of acetic acid, the mixture was concentrated under reduced pressure. To the residue, 10 ml of water and 20 ml of chloroform was added. The oily layer which separated was dried over anhydrous magnesium sulphate, and concentrated under reduced pressure. The residue was purified by column chromatography on silica gel using a mixture of cyclohexane and ethyl acetate (1:4) as eluent to give 96 mg of the title compound having the following physical characteristics.

TLC (cyclohexane:ethyl acetate=1:2): Rf=0.22.
IR: ν=2960, 2930, 2860, 1710, 1460 cm$^{-1}$.
NMR: δ=3.80(3H, s), 3.74(3H, s), 3.15(1H, m), 3.12(2H, d), 1.60–2.14(5H, m), 1.07–1.52(8H, m), 0.87(3H, t).
Mass: m/e=276(M+), 258, 219, 108, 201, 192, 179, 166, 151, 124, 109, 94.

REFERENCE EXAMPLE 17

9α-acetyloxy-11α-(2-tetrahydropyranyloxy)-15-oxo-16RS,18S-ethano-20-ethylprosta-5Z,13E-dienoic acid methyl ester In a flow of argon, to a suspension of 11.3 mg of sodium hydride (content: 64%) in 1 ml of dry tetrahydrofuran, a solution of 88 mg of dimethyl 2-(3S-butylcyclopentyl)-2-oxoethylphosphonate (prepared in Reference Example 16) in 2 ml of dry tetrahydrofuran was added dropwise at −78° C., and the mixture was stirred for 30 min. at same temperature.

To the solution, a solution of 120 mg of 9α-acetyloxy-11α-(2-tetrahydropyranyloxy)-12-formyl-13,14,15,16,17,18,19,20-octanorprost-5Z-enoic acid methyl ester (prepared by the method described in Example 12 in the specification of the United Kingdom Pat. No. 1,482,928) in 2 ml of dry tetrahydrofuran was added dropwise at −78° C., and the mixture was stirred for 2 hrs at the same temperature. After addition of 0.2 ml of acetic acid, the mixture was concentrated under reduced pressure. To the residue was added 20 ml of ethyl acetate and 10 ml of water. The oily layer which separated was washed with water, dried over anhydrous magnesium sulphate and concentrated under reduced pressure. The residue was purified by column chromatography on silica gel using a mixture of cyclohexane and ethyl acetate (4:1) as eluent to give 156 mg of the title compound having the following physical characteristics, in a 94.3% yield.

TLC (cyclohexane:ethyl acetate=2:1): Rf=0.27.
IR: ν=2940, 2860, 1735, 1690, 1665, 1625, 1435 cm.
NMR: δ=6.69(1H, m), 6.25(1H, m), 5.32(2H, m), 5.07(1H, m), 4.56(1H, m), 4.10(1H, m), 3.74(1H, m), 3.65(3H, s), 3.42(1H, m), 3.15(1H, m), 2.05(3H, s), 1.10–2.80 (29H, m), 0.87(3H, t).
Mass: m/e=546(M+), 515, 462, 455, 444, 431, 413, 402, 384, 358, 347, 321, 261, 232, 205, 153, 125, 85.

REFERENCE EXAMPLE 18

9α-acetyloxy-11α-(2-tetrahydropyranyloxy)-15α-hydroxy-16RS,18S-ethano-20-ethylprosta-5Z,13E-dienoic acid methyl ester In a flow of argon, to a solution of 1.1 mg of 3,5-di-t-butyl-4-hydroxytoluene in 4 ml of dry toluene, 1.4 ml of a 1.7M solution of diisobutyl alminium hydride in toluene was added, at −10° C. The mixture was stirred for 15 min at the same temperature, and for 15 min at 15° C. To the solution, a solution of 134 mg of 9α-acetyloxy-11α-(2-tetrahydropyranyloxy)-15-oxo-16RS,18S-ethano-20-ethylprosta-5Z,13Z-dienoic acid methyl ester (prepared in Reference Example 17) in 4 ml of dry toluene was added dropwise at −78° C., and then the mixture was stirred for 3 hrs at the same temperature. After stirring, 1 ml of water was added dropwise to the solution at −15° C. 2 g of anhydrous magnesium sulphate was added to the mixture after stirring for 30 min. at room temperature. The mixture was filtered, and insoluble crystals were washed with ethyl acetate three times. The filtrate and the washings were combined and concentrated under reduced pressure. The residue was purified by column chromatography on silica gel using a mixture of methylene chloride and ethyl acetate (1:1) as eluent to give 107 mg of the title compound having the following physical characteristic.

TLC (cyclohexane:ethyl acetate=2:1): Rf=0.35.

REFERENCE EXAMPLE 19

9α-Acetyloxy-11α,15α-dihydroxy-16RS,18S-ethano-20-ethylprosta-5Z,13E-dienoic acid methyl ester A mixture of 107 mg of 9α-acetyloxy-11α-(2-tetrahydropyranyloxy)-15α-hydroxy-16RS,18S-ethano-20-ethylprosta-5Z,13E-dienoic acid methyl ester (prepared in Reference Example 18), 6 ml of methanol and 30 mg of pyridinium p-toluenesulphonate was stirred for 3 hrs at 50° C. The mixture was concentrated under reduced pressure. To the residue, ethyl acetate was added. The solution was washed with water, dried over anhydrous magnesium sulphate and concentrated under reduced pressure. The residue was purified by column chromatography on silica gel using a mixture of ethyl acetate and cyclohexane as eluent to give 75 mg of the title compound, in a 82.8% yield.

REFERENCE EXAMPLE 20

9α-acetyloxy-11α,15α-dihydroxy-16S,18S-ethano-20-ethylprosta-5Z,13E-dienoic acid methyl ester 75 mg of 9α-acetyloxy-11α,15α-dihydroxy-16RS,18S-ethano-20-ethylprosta-5Z,13E-dienoic acid methyl ester (prepared in Reference Example 19) was purified by Lobar column chromatography (produced by Merck & Co. Ltd.) using a mixture of ethyl acetate and cyclohexane (5:1) as eluent to give 34.5 mg of the title compound having the following physical characteristics.

TLC (ethyl acetate): Rf=0.41.
NMR: δ=5.63(1H, dd), 5.48(1H, dd), 5.33(2H, m) 5.11(1H, m), 3.88(2H, m), 3.65(3H, s), 2.49(1H, m), 2.28(2H, t), 2.05(3H, s), 0.87(3H, m).
Mass: m/e=464(M+), 446, 428, 415, 386, 368, 355, 339, 321, 279, 261, 229, 201.

REFERENCE EXAMPLE 21

9α,11α,15α-trihydroxy-16S,18S-ethano-20-ethylprosta-5Z,13E-dienoic acid methyl ester A mixture of 755 mg of 9α-acetyloxy-11α,15α-dihydroxy-16S,18S-ethano-20-ethylprosta-5Z,13E-dienoic acid methyl ester (prepared in Reference Example 20), 450 mg of anhydrous potassium carbonate and 11 ml of methanol was stirred for 16 hrs at room temperature. The mixture was poured into a mixture of ice-water and 1N hydrochloric acid (1:1). The mixture was extracted with ethyl acetate. The extract was washed with water and a saturated aqueous solution of sodium chloride successively, dried over anhydrous magnesium sulphate and then concentrated under reduced pressure to give 603 mg of the title compound having the following physical characteristics, in a 88% yield.

TLC (ethyl acetate): Rf=0.24;

NMR: $\delta$=5.53(2H, m), 5.40(2H, m), 4.18(1H, m), 3.97(1H, m), 3.83(1H, m), 3.66(3H, s), 2.32(2H, t), 0.88(3H, m).

Mass: m/e=422(M+), 404, 386, 373, 368, 360, 355, 332, 297, 279, 264, 261.

REFERENCE EXAMPLE 22

5RS-bromo-6RS,9α-epoxy-11α,15α-dihydroxy-16S,18S-ethano-20-ethylprost-13E-enoic acid methyl ester A mixture of 603 mg of 9α,11α,15α-trihydroxy-16S,18S-ethano-20-ethylprosta-5Z,13E-dienoic acid methyl ester (prepared in Reference Example 21), 11 ml of refining chloroform, 1.4 ml of tetrahydrofuran and 306 mg of N-bromosuccinimide was stirred for 1.5 hrs at room temperature. To the reaction mixture, 60 ml of diethyl ether was added. The diluted solution was washed with water, and a saturated aqueous solution of sodium chloride, successively, dried over anhydrous magnesium sulphate and concentrated under reduced pressure to give 445 mg of the title compound having the following physical characteristics, in a 62.1% yield.

TLC (ethyl acetate): Rf=0.36.

NMR: $\delta$=5.57(2H, m), 4.55(1H, m), 4.19(1H, m), 2.98(1H, m), 3.84(2H, m), 3.68(3H, s), 0.88(3H, m).

Mass: m/e=482 and 484, 464 and 466, 451 and 453, 438 and 440, 403.

REFERENCE EXAMPLE 23

5RS-bromo-6RS,9α-epoxy-11α,15α-bis(2-tetrahydropyranyloxy)-16S,18S-ethano-20-ethylprost-13E-enoic acid methyl ester To a mixture cooled with ice, of 444 mg of 5RS-bromo-6RS,9α-epoxy-11α,15α-dihydroxy-16S,18S-ethano-20-ethylprost-13E-enoic acid methyl ester (prepared in Reference Example 22), 0.2 ml of 2,3-dihydropyran and 4.2 ml of refining methylene chloride, a catalytic amount of p-toluenesulphonic acid was added, and then the mixture was warmed to room temperature.

After neutralizing with pyridine, diethyl ether was added to the mixture. The diluted solution was washed with 1N hydrochloric acid, water, a saturated aqueous solution of sodium bicarbonate and a saturated aqueous solution of sodium chloride successively, dried over anhydrous magnesium sulphate, and then concentrated under reduced pressure. The residue was purified by column chromatography on silica gel using a mixture of cyclohexane and ethyl acetate (4:1) as eluent to give 535 mg of the title compound having the following physical characteristics, in a 90% yield.

TLC (cyclohexane:ethyl acetate=2:1): Rf=0.53 and 0.46.

Mass: m/e=482 and 484, 464 and 466, 451 and 453, 438 and 440, 403, 402.

REFERENCE EXAMPLE 24

6-oxo-9α-hydroxy-11α,15α-bis(2-tetrahydropyranyloxy)-16S,18S-ethano-20-ethylprost-13E-enoic acid methyl ester A mixture of 134 mg of 5RS-bromo-6RS,9α-epoxy-11α,15α-bis(2-tetrahydropyranyloxy)-16S,18S-ethano-20-ethylprost-13E-enoic acid methyl ester (prepared in Reference Example 23), 0.4 ml of toluene and 0.4 ml of 1,8-diazabicyclo[5.4.0]undecene-7(DBU) was stirred for 30 min at 50° C., for 30 min at 65° C. and 2 hrs at 80° C. successively. The reaction mixture was poured into a mixture of diethyl ether, 1N hydrochloric acid and ice. The oily layer which separated was shaken well with 1N hydrochloric acid. The oily layer was washed with a saturated aqueous solution of sodium bicarbonate and a saturated aqueous solution of sodium chloride successively, dried over anhydrous magnesium sulphate and then concentrated under reduced pressure. The residue was purified by column chromatography on silica gel using a mixture of cyclohexane and ethyl acetate (1:1) as eluent to give 106 mg of the title compound having the following physical characteristics, in a 87.5% yield.

TLC (cyclohexane:ethyl acetate=2:1): Rf=0.12.

Mass: m/e=588, 557, 503, 488, 486, 402.

REFERENCE EXAMPLE 25

6-oxo-9α-hydroxy-11α,15α-bis(2-tetrahydropyranyloxy)-16S,18S-ethano-20-ethylprost-13E-enoic acid A mixture of 106 mg of 6-oxo-9α-hydroxy-11α,15α-bis(2-tetrahydropyranyloxy)-16S,18S-ethano-20-ethylprost-13E-enoic acid methyl ester, 1.6 ml of methanol and 0.4 ml of a 1N aqueous solution of sodium hydroxide was stirred for 16 hrs at room temperature. The mixture was poured into a mixture of 0.5 ml of 1N hydrochloric acid, ice and ethyl acetate. The oily layer which separated was washed with water and a saturated aqueous solution of sodium chloride successively, dried over anhydrous magnesium sulphate and then concentrated under reduced pressure to give 93 mg of the title compound having the following physical characteristic.

TLC (ethyl acetate): Rf=0.21.

REFERENCE EXAMPLE 26

6,9-dioxo-11α,15α-bis(2-tetrahydropyranyloxy)-16S,18S-ethano-20-ethylprost-13E-enoic acid To a mixture cooled to −25° C., of 93 mg of 6-oxo-9α-hydroxy-11α,15α-bis(2-tetrahydropyranyloxy)-16S,18S-ethano-20-ethylprost-13E-enoic acid (prepared in Reference Example 25) and 2 ml of acetone, 0.2 ml of 2.6M Jones reagent was added. The mixture was stirred for 1.5 hrs at the same temperature. To the mixture, isopropanol was added to quench excess oxidizing agent; diethyl ether was added to the mixture. The diluted solution was washed with water and a saturated aqueous solution of sodium chloride successively, dried over anhydrous magnesium sulphate, and then concentrated under reduced pressure. The residue was purified by column chromatography on silica gel using a mixture of cyclohexane and ethyl acetate (1:1) as eluent to give 77 mg of the title compound having the following physical characteristics.

TLC (ethyl acetate): Rf=0.46.

Mass: m/e=488, 404, 386, 279.

EXAMPLE 1

6,9-dioxo-11α,15α-dihydroxy-16S,18S-ethano-20-ethyl-prost-13E-enoic acid.

[i.e. 6-keto-16S,18S-ethano-20-ethyl-PGE$_1$]

A mixture of 76 mg of 6,9-dioxo-11α,15α-bis(2-tetrahydropyranyloxy)-16S,18S-ethano-20-ethylprost-13E-enoic acid (prepared in Reference Example 26), 0.2 ml of tetrahydrofuran and 1.3 ml of a 65% aqueous acetic acid solution was stirred for 10 min at 80° C. To the mixture, 60 ml of ethyl acetate was added, after cooling. The diluted solution was washed with water and a saturated aqueous solution of sodium chloride, dried over anhydrous magnesium sulphate and then concentrated under reduced pressure. The residue was purified by column chromatography on silica gel using a mixture of cyclohexane and ethyl acetate to give 32 mg of the title compound having the following physical characteristics, in a 57.5% yield.

TLC (ethyl acetate): Rf=0.087.
mp: 76°–79° C.
IR (KBr Tablet): $\nu$=3600–2400, 1747, 1728, 1708, 973 cm$^{-1}$.
NMR: $\delta$=5.57(2H, m), 4.09(1H, m), 3.83(1H, m), 2.78(1H, dd), 0.88(3H, m).
Mass: m/e=404, 386, 279.

EXAMPLE 2

α-cyclodextrin clathrate of
6,9-dioxo-11α,15α-dihydroxy-16S,18S-ethano-20-ethyl-prost-13E-enoic acid A solution of 21.6 mg of 6,9-dioxo-11α,15α-dihydroxy-16S,18S-ethano-20-ethylprost-13E-enoic acid (prepared in Example 1) in 3 ml of ethanol was added to a solution of 681 mg of α-cyclodextrin in 6 ml of water. The mixture was stirred at room temperature, and then concentrated under reduced pressure to give 582 mg of the title compound.

The present invention includes within its scope pharmaceutical compositions which comprise the prostaglandin analogue of the formula (III) or a cyclodextrin clathrate thereof or a non-toxic salt thereof, together with a pharmaceutical carrier or coating.

In clinical practice, for use, in the treatment and/or the prevention of diseases induced by platelet aggregation such as thrombosis, or cytodamage, the prostaglandin analogue of the formula (III) or cyclodextrin clathrates thereof or non-toxic salts thereof will normally be administered systemically or partially; usually by oral or parenteral administration.

Solid compositions included in the present invention for oral administration include compressed tablets, pills, dispersible powders and granules. In such solid compositions, one or more of the active compound(s) is, or are, admixed with at least one inert diluent such as lactose, mannitol, glucose, hydroxypropyl cellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, and disintegrating agents, such as cellulose calcium gluconate. The tablets or pills may, if desired, be made into enteric film-coated or gastric film-coated tablets or pills, such as sugar-coated, gelatin-coated, hydroxypropylcellulose-coated or hydroxypropylmethyl-cellulose phthalate-coated tablets or pills; two or more layers may be used. The compositions for oral administration also include capsules of absorbable material such as gelatin.

Liquid compositions included in the present invention for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavouring, perfuming and preserving agents.

Other compositions included in the present invention for oral administration include spray compositions which may be prepared by known methods and which comprise at least one compound of the present invention as active ingredient.

Compositions for parenteral administration by injection included in the present invention include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol and POLYSORBATE 80 (registered Trade Mark).

These compositions may also include adjuvants such as preserving, wetting, emulsifying and dispersing agents. They may be sterilized, for example, by incorporation of sterilizing agents in the compositions or by irradiation. They may also be manufactured in the form of sterile solid compositions which can be dissolved in sterile water or some other sterile injectable medium immediately before use.

Other compositions for parenteral administration include liquids for external use, and endermic liniments such as ointments; suppositories for rectal administration; and pessaries for vaginal administration. Such compositions are prepared by known methods.

The percentage of active ingredient in the compositions of the invention may be varied, it being necessary that it should constitute a proportion such that a suitable dosage for the therapeutic effect desired shall be obtained. Obviously several unit dosage forms may be administered at about the same time. In general, the preparations should normally contain at least 0.025% by weight of active substance when required for administration by injection; for oral administration the preparations will normally contain at least 0.1% by weight of active substance.

The dose to be administered is determined depending upon, for example, age, body weight, symptoms, the desired therapeutic effects, the route of administration, and the duration of the treatment.

In the human adult, for use, in the treatment and/or the prevention of diseases induced by platelet aggregation such as thrombosis, or cytodamage, the doses per person per dose are generally between 0.1 and 500 μg, preferably between 1 and 50 μg by oral administration, and between 0.01 and 50 μg, preferably between 0.1 and 20 μg by parenteral administration, and can be administered up to several times per day.

As mentioned above, the doses to be used depend on various factors. Therefore, there may be cases in which doses greater than the ranges specified above, or lower than the ranges specified above, may be used.

The following Examples illustrate pharmaceutical compositions according to the invention.

EXAMPLE 3

To a mixture of 3 mg of 6-keto-16S,18S-ethano-20-ethyl-PGE$_1$, 100 mg of magnesium stearate, 20 mg of silicon dioxide, 10 mg of talc and 200 mg of cellulose calcium gluconate (CCG), sufficient microcrystalline cellulose was added to obtain 10 g of mixture. After mixing well, the mixture was punched out in conventional manner to obtain 100 tablets each containing 30 μg of the active ingredient.

EXAMPLE 4

3 mg of 6-keto-16S,18S-ethano-20-ethyl-PGE$_1$ and 20.997 g of lactose were mixed and the powder obtained was machine filled into 100 No. 2 hard capsules each containing 30 μg of the active ingredient.

EXAMPLE 5

A solution of 30 mg of 6-keto-16S,18S-ethano-20-ethyl-PGE$_1$ in 10 ml of chloroform was added to 100 ml of MCT (registered Trade Mark; a mixture of triglycerides of fatty acids containing 8 to 10 carbon atoms) and the solution was mixed. After removing chloroform under reduced pressure, the residue was machine filled into 100 soft capsules to give capsules each containing 30 μg of the active ingredient.

EXAMPLE 6

16 mg of α-cyclodextrin clathrate of 6-keto-16S,18S-ethano-20-ethyl-PGE$_1$ (content of active agent: 500 μg) was dissolved in 300 ml of distilled water for injection. The solution was sterilized in conventional manner and placed in 3 ml portions in 5 ml ampoules to obtain 100 ampoules each containing 5 μg of the active ingredient.

We claim:

1. A prostaglandin analogue of the formula:

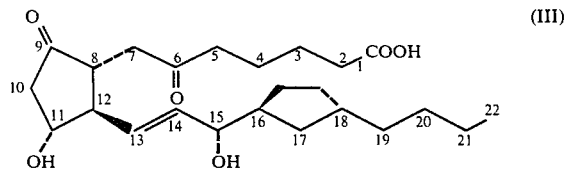

[wherein, the symbol ⌇ represents β-configuration, the dotted line - - - represents α-configuration, and the double bond between $C_{13}$–$C_{14}$ is in trans-configuration] or a cyclodextrin clathrate thereof, or a non-toxic salt thereof.

2. A cyclodextrin clathrate of the prostaglandin analogue according to claim 1.

3. A pharmaceutical composition, useful in the prevention and/or treatment of diseases induced by platelet aggregation, which comprises, as active ingredient, an effective amount of the prostaglandin analogue of the formula (III) depicted in claim 1 wherein the various symbols are as defined in claim 1, or a cyclodextrin clathrate thereof, or a non-toxic salt thereof, in association with a pharmaceutical carrier or coating.

4. A method for the prevention and/or treatment of diseases induced by platelet aggregation in a patient, which comprises administering to the patient an effective amount of the prostaglandin analogue of the formula (III) specified in claim 1, wherein the various symbols are as defined in claim 1, or a cyclodextrin clathrate thereof, or a non-toxic salt thereof.

5. A compound of the formula:

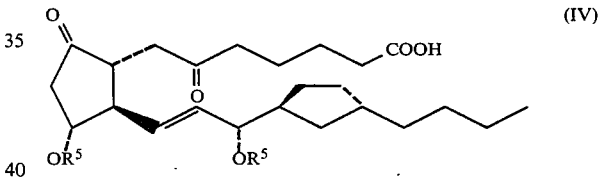

wherein $R^5$ represents a tetrahydropyran-2-yl group or a tetrahydrofuran-2-yl group, each such group being unsubstituted or substituted by at least one alkyl group, or represents a 1-ethoxyethyl group and the other symbols are as defined in claim 1.

* * * * *